(12) United States Patent
Li (10) Patent No.: US 10,571,443 B2
(45) Date of Patent: Feb. 25, 2020

(54) GAS CONCENTRATION DETECTING DEVICE AND DETECTING METHOD THEREOF

(71) Applicant: BOE TECHNOLOGY GROUP CO., LTD., Beijing (CN)

(72) Inventor: Yingyi Li, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 16/138,197

(22) Filed: Sep. 21, 2018

(65) Prior Publication Data

US 2019/0128861 A1 May 2, 2019

(30) Foreign Application Priority Data

Oct. 31, 2017 (CN) .......................... 2017 1 1052997

(51) Int. Cl.
*G01J 4/00* (2006.01)
*G01N 33/00* (2006.01)
*G02B 5/30* (2006.01)

(52) U.S. Cl.
CPC ..... *G01N 33/0027* (2013.01); *G01N 33/0073* (2013.01); *G02B 5/3025* (2013.01)

(58) Field of Classification Search
CPC ......... G01N 21/211; G01N 21/23; G01J 4/04; G01J 4/00
USPC ....................................................... 356/364
See application file for complete search history.

(56) References Cited

U.S. PATENT DOCUMENTS

| 8,575,539 B2 | 11/2013 | Mosley et al. |
| 2003/0129327 A1 | 7/2003 | Shibue et al. |
| 2008/0169758 A1* | 7/2008 | Cok .................... H01L 51/5262 313/506 |
| 2010/0264337 A1 | 10/2010 | Mosley et al. |
| 2012/0034701 A1 | 2/2012 | Hofmann et al. |
| 2012/0162575 A1* | 6/2012 | Lin .................... G02F 1/133514 349/62 |
| 2013/0248736 A1* | 9/2013 | Tkachuk ................. G01N 21/77 250/458.1 |

(Continued)

FOREIGN PATENT DOCUMENTS

| CN | 101576488 A | 11/2009 |
| CN | 104823300 A | 8/2015 |

(Continued)

OTHER PUBLICATIONS

First Chinese Office Action dated Sep. 29, 2019, received for corresponding Chinese Application No. 201711052997.5, 16 pages.

*Primary Examiner* — Md M Rahman
(74) *Attorney, Agent, or Firm* — Kinney & Lange, P.A.

(57) ABSTRACT

A gas concentration detecting device and a detecting method thereof are provided. The gas concentration detecting device includes: a first polarizer; a second polarizer arranged opposite to the first polarizer in such a way that a gap is formed between the first polarizer and the second polarizer; a light source on a side of the second polarizer away from the first polarizer or on a side of the first polarizer away from the second polarizer; and a photoluminescent layer between the first polarizer and the second polarizer. The light transmission axis of the first polarizer is perpendicular to a light transmission axis of the second polarizer.

19 Claims, 4 Drawing Sheets

(56) References Cited

U.S. PATENT DOCUMENTS

| | | | |
|---|---|---|---|
| 2014/0004304 A1* | 1/2014 | Yu | B82Y 20/00 |
| | | | 428/144 |
| 2014/0240627 A1* | 8/2014 | Wu | G02F 1/1323 |
| | | | 349/16 |
| 2016/0020425 A1 | 1/2016 | Meyer et al. | |

FOREIGN PATENT DOCUMENTS

| | | | | |
|---|---|---|---|---|
| FR | 2340540 A2 | | 9/1977 | |
| KR | 20180063415 A | * | 6/2018 | ....... G02F 1/133617 |

\* cited by examiner

GAS CONCENTRATION DETECTING DEVICE AND DETECTING METHOD THEREOF

CROSS-REFERENCE TO RELATED APPLICATION

This application claims priority of Chinese Patent Application No. 201711052997.5 filed on Oct. 31, 2017 in China National Intellectual Property Administration, the disclosure of which is incorporated herein by reference in entirety.

BACKGROUND

Technical Field

Embodiments of the present disclosure relate to the field of detection technology, and in particular, to a gas concentration detecting device and a detecting method of the gas concentration detecting device.

Description of the Related Art

With the rapid development of social economy and the increasing living standards of people, people are paying more and more attention to industrial safety and living environments. Therefore, it is increasingly important to detect concentration of gas in an environment where people live. Especially in a chemical workshop, it is common to generate a large amount of gas during the manufacture of some products. If these gases accumulate and reach a certain concentration, they will harm the bodily health of staff to some extent, and even threaten life safety of the staff, incurring some irreparable damage. Therefore, it is an important measure for preventing losses and protecting personal safety to detect gas concentration.

SUMMARY

Embodiments of the present disclosure provide a gas concentration detecting device and a detecting method thereof.

In one aspect, there is provided a gas concentration detecting device, comprising:

a first polarizer;

a second polarizer arranged opposite to the first polarizer in such a way that a gap is formed between the first polarizer and the second polarizer;

a light source on a side of the second polarizer away from the first polarizer or on a side of the first polarizer away from the second polarizer; and a photoluminescent layer between the first polarizer and the second polarizer, wherein a light transmission axis of the first polarizer is perpendicular to a light transmission axis of the second polarizer.

In an embodiment, the gap is configured to accommodate gases therein, and the photoluminescent layer is photoexcited to have a luminescent intensity which is proportional to a concentration of a gas to be detected in the gases accommodated in the gap.

In an embodiment, the gas concentration detecting device further comprises a seal ring, wherein the first polarizer, the second polarizer and the seal ring constitute a closed chamber.

In an embodiment, an air inlet and an air outlet are provided on the closed chamber.

In an embodiment, the air inlet and the air outlet are provided on the seal ring.

In an embodiment, the seal ring is provided at an edge of the first polarizer or an edge of the second polarizer.

In an embodiment, the seal ring is made from frame sealing adhesive.

In an embodiment, the photoluminescent layer is made from a phosphor of pyrenes dye in response to a gas to be detected being oxygen.

In an embodiment, the photoluminescent layer is made from a phosphor of metal porphyrin in response to a gas to be detected being ammonia gas.

In an embodiment, the light source is a light emitting device of OLED.

In an embodiment, the gas concentration detecting device further comprises an encapsulation layer for encapsulating the light emitting device of OLED, and the second polarizer is disposed on the encapsulation layer.

In an embodiment, at least one of the first polarizer and the second polarizer is a metal wire gating polarizer.

In an embodiment, at least one of the first polarizer and the second polarizer is an iodine-based or dye-based polarizer, and wherein the gas concentration detecting device further comprises a base substrate on which the iodine-based or dye-based polarizer is disposed.

In an embodiment, the gas concentration detecting device further comprises a detector disposed on a side of the first polarizer and the second polarizer away from the light source for detecting an intensity value of light emitted from the first polarizer or the second polarizer.

In an embodiment, the gas concentration detecting device further comprises a processor, wherein the processor is connected to the detector for acquiring a concentration of a gas to be detected in gases accommodated in the gap between the first polarizer and the second polarizer according to the intensity value of the light detected by the detector.

In another aspect, there is provided a detecting method of the gas concentration detecting device according to any one of the above embodiments, comprising:

controlling the light source to emit light and obtaining a concentration of a gas to be detected in gases accommodated in the gap between the first polarizer and the second polarizer according to an intensity of light emitted from the first polarizer or the second polarizer.

In an embodiment, before the controlling the light source to emit light and obtaining the concentration of the gas to be detected in the gases accommodated in the gap between the first polarizer and the second polarizer according to the intensity of the light emitted from the first polarizer or the second polarizer, the method further comprises:

introducing a gas into the gap between the first polarizer and the second polarizer.

In an embodiment, before the controlling the light source to emit light and obtaining the concentration of the gas to be detected in the gases accommodated in the gap between the first polarizer and the second polarizer according to the intensity of the light emitted from the first polarizer or the second polarizer, the method further comprises:

detecting the intensity value of the light emitted from the first polarizer or the second polarizer.

In an embodiment, before the controlling the light source to emit light and obtaining the concentration of the gas to be detected in the gases accommodated in the gap between the first polarizer and the second polarizer according to the intensity of the light emitted from the first polarizer or the second polarizer, the method further comprises:

providing the photoluminescent layer comprising a phosphor of pyrenes dye, or providing the photoluminescent layer comprising a phosphor of metal porphyrin.

In an embodiment, before the introducing the gas into the gap between the first polarizer and the second polarizer, the method further comprises:

discharging a gas in the gap between the first polarizer and the second polarizer.

BRIEF DESCRIPTION OF THE DRAWINGS

In order to more clearly illustrate embodiments of the present disclosure or technical solutions in the related art, the drawings to be used in the description of the embodiments or the related art will be briefly described below. Obviously, the drawings in the following description merely represent some embodiments of the present disclosure, other drawings may be obtained by those skilled in the art from these drawings without creative efforts.

DETAILED DESCRIPTION OF EMBODIMENTS

Below, the technical solutions in the embodiments of the present disclosure will be clearly and completely described with reference to the drawings in the embodiments of the present disclosure. It is apparent that the described embodiments merely represent a part of embodiments of the present disclosure, rather than all of the embodiments. All other embodiments which are obtained by those skilled in the art based on the embodiments of the present disclosure without creative efforts fall within the scope of the present disclosure.

Figure 1:
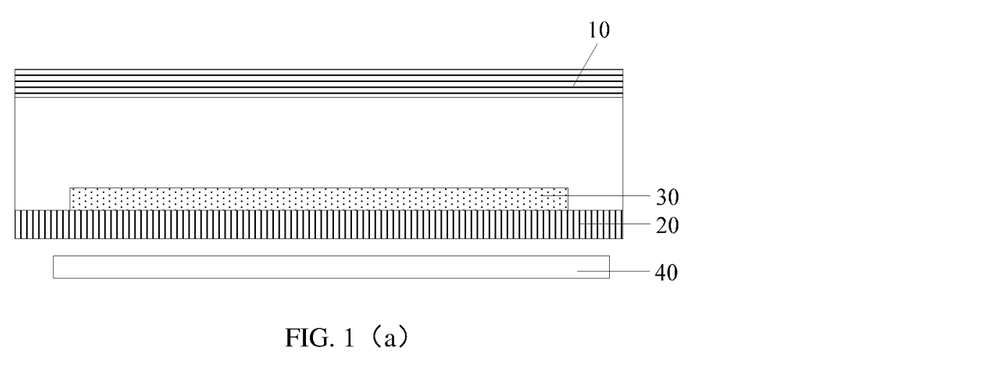
FIG. 1(a) is a schematic structural view of a gas concentration detecting device according to an embodiment of the present disclosure.
FIG. 1(b) is a schematic structural view of a gas concentration detecting device according to an embodiment of the present disclosure.
FIG. 1(c) is a schematic structural view of a gas concentration detecting device according to an embodiment of the present disclosure.

An embodiment of the present disclosure provides a gas concentration detecting device, as shown in FIG. 1(a), FIG. 1(b), and FIG. 1(c), including: a first polarizer 10 and a second polarizer 20 disposed opposite to each other; and a photoluminescent layer 30 disposed between the first polarizer 10 and the second polarizer 20. A gap is formed between the first polarizer 10 and the second polarizer 20 for accommodating gases, and the photoluminescent layer 30 is photoexcited to have a luminescent intensity which is proportional to a concentration of a gas to be detected in the gases accommodated in the gap. The gas concentration detecting device further includes: a light source 40 disposed on a side of the second polarizer 20 away from the first polarizer 10, wherein a light transmission axis of the first polarizer 10 is perpendicular to a light transmission axis of the second polarizer 20.

Figure 2A:
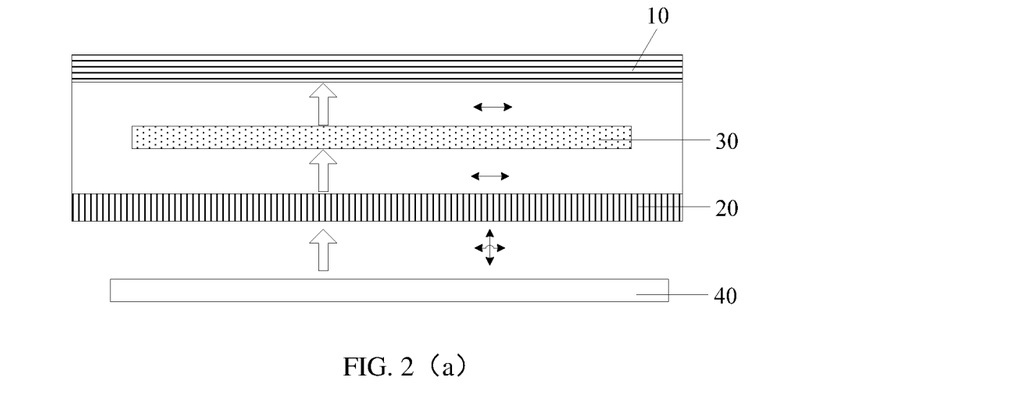
FIG. 2(a) is a schematic view of a photoluminescent layer in a gas concentration detecting device according to an embodiment of the present disclosure in a state of non luminance.
Figure 2B:
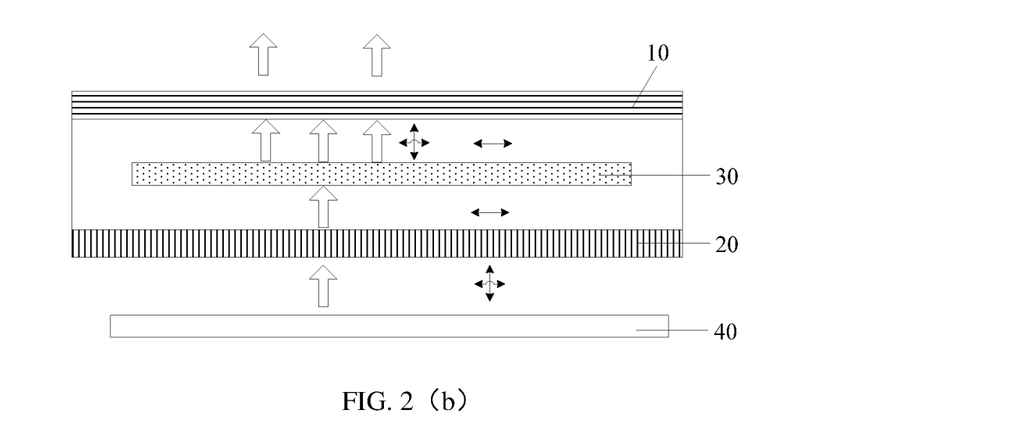
FIG. 2(b) is a schematic view of a photoluminescent layer in a gas concentration detecting device according to an embodiment of the present disclosure in a state of luminance.

The principle that the gas concentration detecting device according to the embodiment of the present disclosure detects a gas concentration will be described below. A natural light emitted by the light source 40 is converted into a polarized light through the second polarizer 20. Since the light transmission axis of the first polarizer 10 is perpendicular to the light transmission axis of the second polarizer 20, the polarized light which has passed through the second polarizer 20 cannot transmit through the first polarizer 10. As shown in FIG. 2(a), if the photoluminescent layer 30 does not emit light, then there is no light to be emitted from the first polarizer 10. As shown in FIG. 2(b), if the photoluminescent layer 30 emits light under an excitation of the light emitted by the light source 40, then, since the light emitted by the photoluminescent layer 30 is natural light, not polarized light, the light with a polarization direction which is the same as the light transmission axis of the first polarizer 10 can transmit through the first polarizer 10. In this way, the light emitted by the light source 40 and the light excited by the photoluminescent layer 30 can be distinguished by the first polarizer 10 and the second polarizer 20 (the light emitted by the light source 40 cannot transmit through the first polarizer 10, and the light emitted by the photoluminescent layer 30 can transmit through the first polarizer 10). In addition, since the photoluminescent layer 30 is photoexcited to have a luminescent intensity which is proportional to the concentration of the gas to be detected in the gases accommodated in the gap, the concentration of the gas to be detected in the gases accommodated in the gap can be obtained according to the intensity of the light emitted from the first polarizer 10.

It should be noted that, firstly, the photoluminescent layer 30 may be disposed on the second polarizer 20 and in contact with the second polarizer 20 as shown in FIG. 1(a). In this case, there is a gap between the first polarizer 10 and the photoluminescent layer 30. Alternatively, the photoluminescent layer 30 may also be disposed on the first polarizer 10 and in contact with the first polarizer 10 as shown in FIG. 1(b). In this case, there is a gap between the second polarizer 20 and the photoluminescent layer 30. Of course, the photoluminescent layer 30 may also be disposed between the first polarizer 10 and the second polarizer 20 as shown in FIG. 1(c), and there are gaps between the photoluminescent layer 30 and the first polarizer 10 and between the photoluminescent layer 30 and the second polarizer 20. It should be understood by those skilled in the art that the photoluminescent layer 30 should be disposed on a transparent substrate.

Based on the above, in order to reduce the difficulty of manufacturing process of the gas concentration detecting device, in the embodiment of the present disclosure, as shown in FIG. 1(a) and FIG. 1(b), the photoluminescent layer 30 is disposed on the first polarizer 10 or the second polarizer 20. In addition, when the photoluminescent layer 30 is disposed on the first polarizer 10 or the second polarizer 20, the photoluminescent layer 30 may be directly disposed on the first polarizer 10 or the second polarizer 20, so that it is in contact with the first polarizer 10 or the second polarizer 20. Alternatively, a passivation layer is firstly disposed on the first polarizer 10 or the second polarizer 20, and the photoluminescent layer 30 is then disposed on the passivation layer.

Secondly, a support member may be disposed between the first polarizer 10 and the second polarizer 20 to allow a gap between the first polarizer 10 and the second polarizer 20.

In addition, the gap between the first polarizer 10 and the second polarizer 20 may be in communication with the external environment, such that the concentration of the gas to be detected in the gases accommodated in the gap is detected, thereby the concentration of the gas to be detected in the external environment is detected. The gap between the first polarizer 10 and the second polarizer 20 may also be sealed and not be in communication with the external environment, which will not be limited herein.

Thirdly, the concentration of the gas to be detected in the gases accommodated in the gap refers to a ratio of the gas to be detected accommodated in the gap to the gases accommodated in the gap, and the ratio may be in a form of a mass percentage, a volume percentage or a mole percentage. As an example, the gas to be detected is oxygen and the gases accommodated in the gap are mixed gases, then the concentration of the oxygen accommodated in the gap is a percentage of oxygen in the mixed gases. For example, if the concentration of the oxygen accommodated in the gap is 100%, then only oxygen is accommodated in the gap. For another example, if the concentration of the oxygen accommodated in the gap is 60%, and the oxygen accommodated in the gap accounts for 60% of the mixed gases.

Fourthly, the photoluminescent layer 30 is photoexcited to have a luminescent intensity which is proportional to the concentration of the gas to be detected in the gases accommodated in the gap. The luminescent intensity may be inversely proportional to the concentration of the gas to be detected in the gases accommodated in the gap, that is, the larger the concentration of the gas to be detected in the gases accommodated in the gap is, the smaller the intensity of the light emitted by the photoluminescent layer 30 after the photoexcitation is. Alternatively, it may be in a direct proportional relationship, that is, the larger the concentration of the gas to be detected in the gases accommodated in the gap is, the larger the intensity of the light emitted by the photoluminescent layer after the photoexcitation is.

Fifthly, the gas concentration detecting device according to the embodiments of the present disclosure may be used to detect concentrations of different types of gases, specifically depending on the materials of the photoluminescent layer 30. Herein, it is not intended to limit the materials of the photoluminescent layer 30 which is specifically related to the gas to be detected, and gas concentrations of different gases may be detected by changing the materials of the photoluminescent layer 30. For example, when the gas concentration detecting device is used to detect the concentration of oxygen, that is, the gas to be detected is oxygen, the materials of the photoluminescent layer 30 may be a phosphor of pyrenes dye, because the phosphor of pyrenes dye cannot be excited to emit light in a pure oxygen environment, and the intensity of the light emitted by the phosphor of pyrenes dye changes as the oxygen concentration in the gas environment changes. Specifically, the smaller the oxygen concentration is, the larger the intensity of the light emitted by the phosphor of pyrenes dye after the photoexcitation is. Based on this, the concentration of oxygen in the gases accommodated in the gap may be obtained according to the intensity of the light transmitted through the first polarizer 10. The reason why the intensity of the light emitted by the phosphor of pyrenes dye after the photoexcitation changes as the oxygen concentration changes, lies in that the oxygen reacts with luminophores in the phosphor of pyrenes dye to generate a non-luminescent substance. Therefore, if the oxygen concentration is higher, more luminophores in the phosphor of pyrenes dye react with the oxygen, so that the intensity of the light emitted by the phosphor of pyrenes dye is reduced.

For another example, when the gas concentration detecting device is used to detect the concentration of ammonia gas, that is, the gas to be detected is ammonia gas, the material of the photoluminescent layer 30 may be a phosphor of metal porphyrin. The phosphor of metal porphyrin cannot be excited to emit light in a pure ammonia environment, and the intensity of the light emitted by the phosphor of metal porphyrin changes as the ammonia gas concentration in the gas environment changes.

Sixthly, the type of the light source 40 is not limited. The light source 40 may be an LED (Light Emitting Diode) lamp, or a light emitting device of OLED (Organic Light Emitting Diode). Of course, it may also be an incandescent lamp, a tungsten halogen lamp, or the like. Since the light emitting device of OLED has a small thickness, the volume of the gas concentration detecting device can be reduced, and the brightness of the light emitted by the light emitting device of OLED is increased. Thus, in one embodiment, the light source 40 is a light emitting device of OLED.

The embodiment of the present disclosure provides a gas concentration detecting device including the first polarizer 10 and the second polarizer 20, and the light transmission axis of the first polarizer 10 is perpendicular to the light transmission axis of the second polarizer 20, therefore the polarized light that has passed through the second polarizer 20 cannot transmit through the first polarizer 10. However, the light emitted by the photoluminescent layer 30 under the excitation of the light source 40 is natural light, thus the light having the same polarization direction as the first polarizer 10 can be emitted from the first polarizer 10. Since the intensity of the light emitted by the photoluminescent layer 30 under the excitation of the light source 40 is proportional to the concentration of the gas to be detected in the gases accommodated in the gap, the concentration of the gas to be detected in the gases accommodated in the gap can be obtained according to the intensity of the light emitted from the first polarizer 10.

Figure 3:
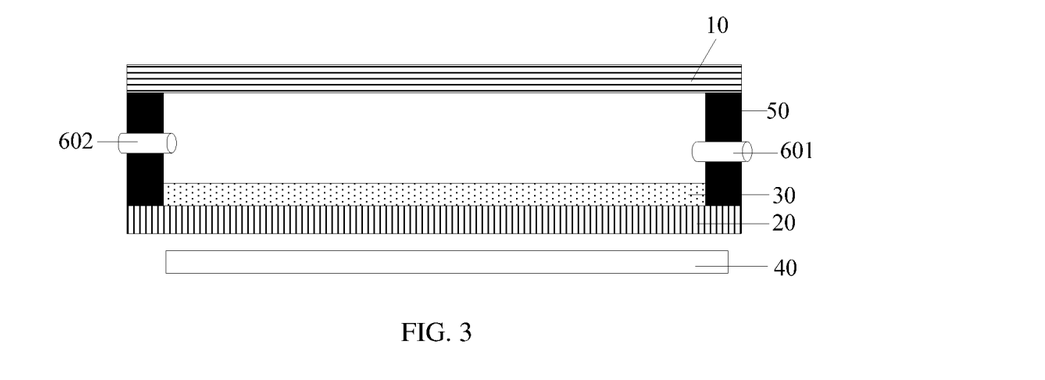
FIG. 3 is a schematic structural view of a gas concentration detecting device according to an embodiment of the present disclosure.

If the gap between the first polarizer 10 and the second polarizer 20 is in communication with the external environment, the composition of the gases accommodated in the gap is the same as that of the external environment. In this case, the gas concentration detecting device can only be used to detect the concentration of the gas to be detected in the external environment, thereby limiting the range of application of the gas concentration detecting device. In view of this, as an example, as shown in FIG. 3, the gas concentration detecting device may further include a seal ring 50 disposed at an edge of the first polarizer 10 or an edge of the second polarizer 20, and the first polarizer 10, the second polarizer 20 and the seal ring 50 constitute a closed chamber. The closed chamber is provided with an air inlet 601 and an air outlet 602.

The materials of the seal ring 50 are not limited, for example, it may be rubber or frame sealing adhesive.

Since the frame sealing adhesive has good sealing property and the frame sealing adhesive can attach the first polarizer 10 and the second polarizer 20 together. Based on this, the process of coating the frame sealing adhesive may be the same as that in a display device in the related art, therefore the frame sealing adhesive may be coated by using the existing equipments, thereby improving the utilization rate of the production line. Thus, the material of the seal ring 50 in the embodiments of the present disclosure may be a frame sealing adhesive. When the material of the seal ring 50 is chosen from frame sealing adhesive, it is possible to coat a round of frame sealing adhesive at the edge of the first polarizer 10, and then to assemble the second polarizer 20 to the first polarizer 10, and then to cure the frame sealing adhesive so as to fix the first polarizer 10 and the second polarizer 20 together. Of course, it is possible to coat a round of frame sealing adhesive at the edge of the second polarizer 20, and then to implement steps similar to those described above, the steps will not be described again. The first polarizer 10, the second polarizer 20 and the frame sealing adhesive constitute a closed chamber, and the height of the closed chamber is related to the thickness of the coated frame sealing adhesive. Herein, the materials of the frame sealing adhesive may be a thermosetting resin or an ultra-violet curable resin.

Herein, arrangement positions of the air inlet 601 and the air outlet 602 are not limited in the present disclosure. They may be disposed on the first polarizer 10 or the second polarizer 20, or may be disposed on the seal ring 50, but they are not limited thereto. Since the light emitted from the light source 40 needs to be directed to the second polarizer 20 and the light emitted from the photoluminescent layer 30 needs to be emitted out from the first polarizer 10, the air inlet 601 and the air outlet 602 are disposed on the seal ring 50 in the embodiment of the present disclosure so as not to block the light and thereby affect detection precision of the gas concentration detecting device. In addition, an air inlet tube may be disposed on the air inlet 601 and an air outlet tube may be disposed on the air outlet 602 to facilitate introducing the gas into the closed chamber or discharging the gas from the closed chamber.

It should be noted that the first polarizer 10, the second polarizer 20 and the seal ring 50 constitute a closed chamber. When it is required to detect the concentration of the gas to be detected in the gases, the original gases in the closed chamber is firstly discharged through the air outlet 602, and then the gases to be detected are introduced into the closed chamber through the air inlet 601, so as to detect the concentration of the gas to be detected in the gases. The introduction and discharging of the gas may be performed simultaneously.

In the embodiment of the present disclosure, the first polarizer 10, the second polarizer 20 and the seal ring 50 constitute a closed chamber, so that any gases to be detected can be introduced into the closed chamber to detect the concentration of the gas to be detected in the gases. In this way, the range of application of the gas concentration detecting device is extended, and the affection of the gases in the external environment on the composition of the gas in the closed chamber is avoided, thereby the concentration of the gas to be detected by the gas concentration detecting device becomes more accurate.

Figure 4:
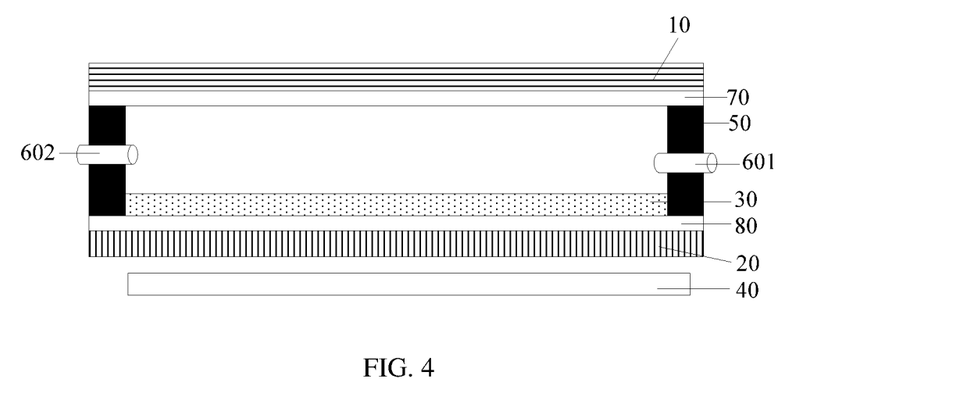
FIG. 4 is a schematic structural view of a gas concentration detecting device according to an embodiment of the present disclosure.

Since the thickness of the polarizer is reduced, in order to prevent the polarizer from being damaged, in an embodiment of the present disclosure, the first polarizer 10 is disposed on a first base substrate 70 and the second polarizer 20 is disposed on a second base substrate 80, as shown in FIG. 4. Herein, if the photoluminescent layer 30 is disposed on the second polarizer 20, the second polarizer 20 and the photoluminescent layer 30 may be respectively disposed on both sides of the second base substrate 80, or they may be disposed on one side of the second base substrate 80. Specifically, the second polarizer 20 may be firstly formed on the second base substrate 80, and then the photoluminescent layer 30 may be formed on the second polarizer 20.

Figure 5:
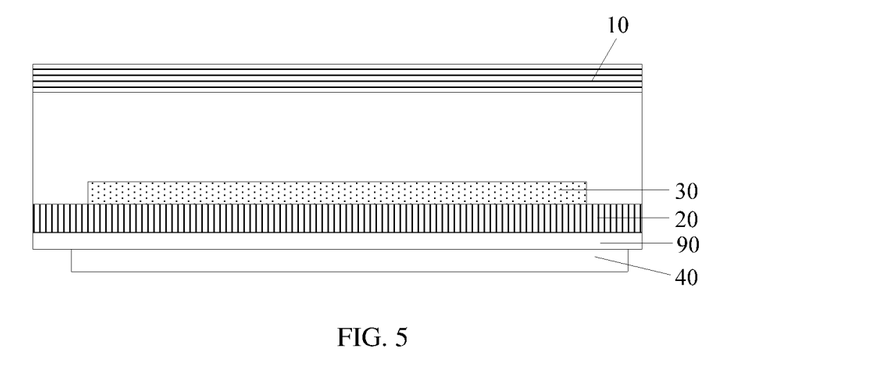
FIG. 5 is a schematic structural view of a gas concentration detecting device according to an embodiment of the present disclosure.

As an example, if the light source 40 is a light emitting device of OLED, the gas concentration detecting device further includes an encapsulation layer 90 for encapsulating the light emitting device of OLED, and the second polarizer 20 is disposed on the encapsulation layer 90, as shown in FIG. 5.

The material of the encapsulation layer 90 is not limited in the present disclosure, and it may be an inorganic material or an organic material. As an example, the encapsulation layer 90 is made from an inorganic material, specifically, for example, silicon nitride ($SiN_x$), silicon oxide ($SiO_x$), silicon oxynitride ($SiO_xN_y$) or the like. On basis of this, the encapsulation layer 90 may be of one layer, or two or more layers.

In the previous embodiment of the present disclosure, it is necessary to dispose the second polarizer 20 on a base substrate. Since the second polarizer 20 is disposed on the encapsulation layer 90 in this embodiment of the present disclosure, the encapsulation layer 90 can function the same as the base substrate. Thus, it is no longer necessary to provide the base substrate, thus eliminating the usage of one base substrate and reducing the thickness of the gas concentration detecting device.

In the embodiments of the present disclosure, it is not intended to limit the types of the first polarizer 10 and the second polarizer 20, and they may be selected as needed. In addition, the types of the first polarizer 10 and the second polarizer 20 may be the same or different. For example, the first polarizer 10 and/or the second polarizer 20 are/is a metal wire gating polarizer. Herein, the first polarizer 10 may be a metal wire gating polarizer, and the second polarizer 20 may be other types of polarizers; alternatively, the second polarizer 20 may be a metal wire gating polarizer, and the first polarizer 10 may be other types of polarizers; of course, the first polarizer 10 and the second polarizer 20 each may be a metal wire gating polarizer.

For another example, the first polarizer 10 and/or the second polarizer 20 are/is an iodine-based or dye-based polarizer. If the first polarizer 10 and/or the second polarizer 20 are/is an iodine-based or dye-based polarizer, as shown in FIG. 4, the gas concentration detecting device further includes a base substrate, and the iodine-based or dye-based polarizer is disposed on the base substrate. In FIG. 4, as an example, both the first polarizer 10 and the second polarizer 20 are iodine-based or dye-based polarizers, the first polarizer 10 is disposed on the first base substrate 70 and the second polarizer 20 is disposed on the second base substrate 80.

Figure 6:
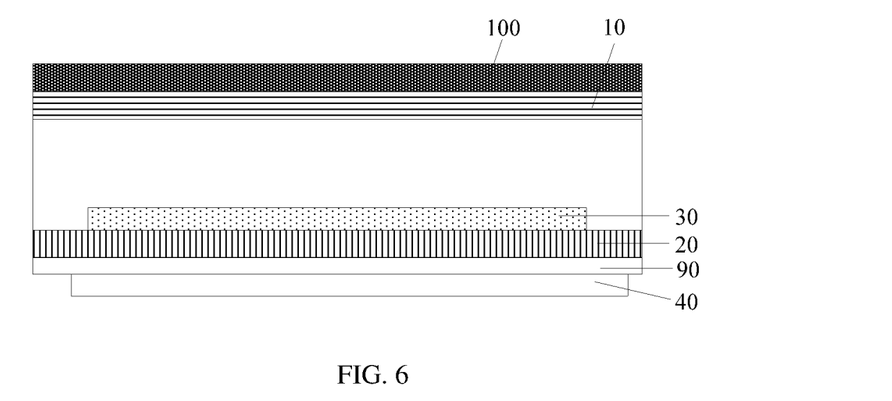
FIG. 6 is a schematic structural view of a gas concentration detecting device according to an embodiment of the present disclosure.

As an example, as shown in FIG. 6, the gas concentration detecting device further includes a detector 100 disposed on a side of the first polarizer 10 away from the second polarizer 20 for detecting an intensity value of the light emitted from the first polarizer 10.

The type of the detector 100 is not limited in the present disclosure, as long as the intensity value of the light emitted from the first polarizer 10 can be detected. By way of example, the detector 100 may be a photoelectric detection device.

In the embodiment of the present disclosure, the detector 100 is disposed on the side of the first polarizer 10 away from the second polarizer 20. In this way, the intensity value of the light emitted from the first polarizer 10 can be accurately detected, so that the achieved concentration of the gas to be detected in the gases accommodated in the gap between the first polarizer 10 and the second polarizer 20 is more accurate.

Figure 7:
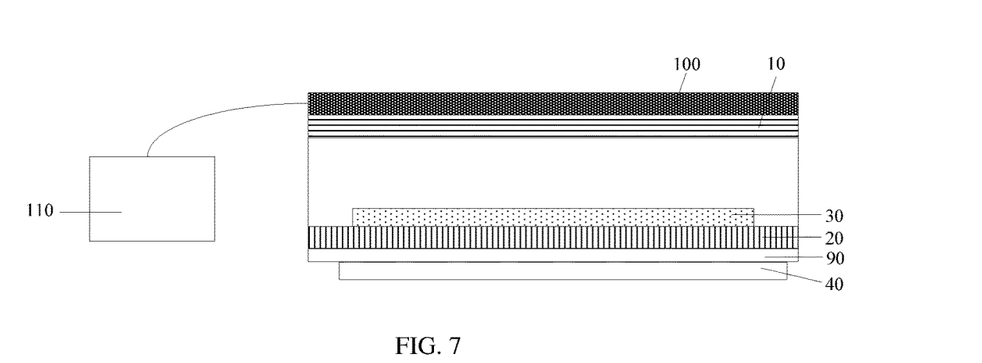
FIG. 7 is a schematic structural view of a gas concentration detecting device according to an embodiment of the present disclosure.

As another example, as shown in FIG. 7, the gas concentration detecting device further includes a processor 110 connected to the detector 100 for acquiring the concentration of the gas to be detected in the gases accommodated in the gap between the first polarizer 10 and the second polarizer 20 according to the intensity value of the light detected by the detector 100.

Herein, the processor 110 may be, for example, a CPU (Central Processing Unit).

In the embodiment of the present disclosure, the gas concentration detecting device further includes a processor 110. Since the processor 110 is configured to acquire the concentration of the gas to be detected in the gases accommodated in the gap between the first polarizer 10 and the second polarizer 20 according to the intensity value of the light detected by the detector 100, the concentration of the gas to be detected in the gases accommodated in the gap between the first polarizer 10 and the second polarizer 20 can be accurately obtained, thereby facilitating the user to make relevant measures according to the concentration of the gas to be detected.

In the above embodiments, if the material of the photoluminescent layer 30 is a phosphor of pyrenes dye, the gas concentration detecting means is an oxygen concentration detecting device for detecting the concentration of the oxygen in the gases accommodated in the gap between the first polarizer 10 and the second polarizer 20; if the material of the photoluminescent layer 30 is a phosphor of metal porphyrin, the gas concentration detecting device is an ammonia gas concentration detecting device for detecting the concentration of the ammonia gas in the gases accommodated in the gap between the first polarizer 10 and the second polarizer 20.

An embodiment of the present disclosure further provides a detecting method of the above gas concentration detecting device, including:

S100: controlling the light source 40 to emit light and obtaining a concentration of the gas to be detected in the gases accommodated in the gap between the first polarizer 10 and the second polarizer 20 according to the intensity of the light emitted from the first polarizer 10.

Herein, the type of the light source 40 is not limited. The light source 40 may be an LED lamp, or a light emitting device of OLED. Of course, it may also be an incandescent lamp, a tungsten halogen lamp, or the like. In one embodiment, the light source 40 is a light emitting device of OLED.

Herein, the gap between the first polarizer 10 and the second polarizer 20 may be in communication with the external environment, or it may also be closed and be not in communication with the external environment, which will not be limited. If the gap between the first polarizer 10 and the second polarizer 20 is in communication with the external environment, the gases accommodated in the gap between the first polarizer 10 and the second polarizer 20 are the gases in the external environment; if the gap between the polarizer 10 and the second polarizer 20 is closed, any gases to be detected may be introduced into the gap between the first polarizer 10 and the second polarizer 20, so as to detect the concentration of the gas to be detected in these gases.

The embodiment of the present disclosure provides a detecting method of the gas concentration detecting device including the first polarizer 10 and the second polarizer 20, and the light transmission axis of the first polarizer 10 is perpendicular to the light transmission axis of the second polarizer 20, therefore the polarized light that has passed through the second polarizer 20 cannot transmit through the first polarizer 10. However, the light emitted by the photoluminescent layer 30 under the excitation of the light source 40 is natural light, thus the light having the same polarization direction as the first polarizer 10 can be emitted from the first polarizer 10. Since the intensity of the light emitted by the photoluminescent layer 30 under the excitation of the light source 40 is proportional to the concentration of the gas to be detected in the gases accommodated in the gap, the concentration of the gas to be detected in the gases accommodated in the gap can be obtained according to the intensity of the light emitted from the first polarizer 10.

As an example, before controlling the light source 40 to emit light and obtaining the concentration of the gas to be detected in the gases accommodated in the gap between the first polarizer 10 and the second polarizer 20 according to the intensity of the light emitted from the first polarizer 10, the method further includes:

introducing a gas into the gap between the first polarizer 10 and the second polarizer 20.

Herein, the gas that is introduced into the gap between the first polarizer 10 and the second polarizer 20 is not limited in the present disclosure, and it may be any kind of gas. The gas composition may be the same as or different from the gas composition of the external environment.

In the embodiment of the present disclosure, the gas is introduced into the gap between the first polarizer 10 and the second polarizer 20, so that the concentration of the gas to be detected in the gas can be detected.

As an example, before obtaining the concentration of the gas to be detected in the gases accommodated in the gap between the first polarizer 10 and the second polarizer 20 according to the intensity of the light emitted from the first polarizer 10, the method further includes:

detecting an intensity value of the light emitted from the first polarizer 10.

Here, a photoelectric detection device may be disposed on the first polarizer 10 to detect the intensity value of the light emitted from the first polarizer 10.

In the embodiment of the present disclosure, since the intensity value of the light emitted from the first polarizer 10 is detected, the intensity of the light emitted from the first polarizer 10 can be accurately detected. In this way, the achieved concentration of the gas to be detected in the gases accommodated in the gap between the first polarizer 10 and the second polarizer 20 is more accurate.

The above description only refers to some specific embodiments of the present disclosure, but the scope of the present disclosure is not limited thereto. Changes or substitutions may be readily made by those skilled in the art within the technical scope of the present disclosure, and such changes or substitutions should be covered within the scope of the present disclosure. Therefore, the scope of the present disclosure should be defined by the scope of the appending claims.

What is claimed is:

1. A gas concentration detecting device, comprising:
   a first polarizer;
   a second polarizer arranged opposite to the first polarizer in such a way that a gap is formed between the first polarizer and the second polarizer; a light source on a side of the second polarizer away from the first polarizer or on a side of the first polarizer away from the second polarizer; and a photoluminescent layer between the first polarizer and the second polarizer, wherein a light transmission axis of the first polarizer is perpendicular to a light transmission axis of the second polarizer;

wherein the gap is configured to accommodate gases therein, and the photoluminescent layer is photoexcited to have a luminescent intensity which is proportional to a concentration of a gas to be detected in the gases accommodated in the gap.

2. The gas concentration detecting device according to claim 1, further comprising a seal ring, wherein the first polarizer, the second polarizer and the seal ring constitute a closed chamber.

3. The gas concentration detecting device according to claim 2, wherein an air inlet and an air outlet are provided on the closed chamber.

4. The gas concentration detecting device according to claim 3, wherein the air inlet and the air outlet are provided on the seal ring.

5. The gas concentration detecting device according to claim 2, wherein the seal ring is provided at an edge of the first polarizer or an edge of the second polarizer.

6. The gas concentration detecting device according to claim 2, wherein the seal ring is made from frame sealing adhesive.

7. The gas concentration detecting device according to claim 1, wherein the photoluminescent layer is made from a phosphor of pyrenes dye and a gas to be detected is oxygen.

8. The gas concentration detecting device according to claim 7, wherein the photoluminescent layer is made from a phosphor of metal porphyrin and a gas to be detected is ammonia gas.

9. The gas concentration detecting device according to claim 7, wherein the light source is a light emitting device of OLED.

10. The gas concentration detecting device according to claim 9, further comprising an encapsulation layer for encapsulating the light emitting device of OLED, and the second polarizer is disposed on the encapsulation layer.

11. The gas concentration detecting device according to claim 7, wherein at least one of the first polarizer and the second polarizer is a metal wire gating polarizer.

12. The gas concentration detecting device according to claim 7, wherein at least one of the first polarizer and the second polarizer is an iodine-based or dye-based polarizer, and
wherein the gas concentration detecting device further comprises a base substrate on which the iodine-based or dye-based polarizer is disposed.

13. The gas concentration detecting device according to claim 7, further comprising a detector disposed on a side of the first polarizer and the second polarizer away from the light source for detecting an intensity value of light emitted from the first polarizer or the second polarizer.

14. The gas concentration detecting device according to claim 13, further comprising a processor,
wherein the processor is connected to the detector for acquiring a concentration of a gas to be detected in gases accommodated in the gap between the first polarizer and the second polarizer according to the intensity value of the light detected by the detector.

15. A detecting method of the gas concentration detecting device according to claim 7, comprising:
controlling the light source to emit light and obtaining a concentration of a gas to be detected in gases accommodated in the gap between the first polarizer and the second polarizer according to an intensity of light emitted from the first polarizer or the second polarizer.

16. The detecting method according to claim 15, wherein, before the controlling the light source to emit light and obtaining the concentration of the gas to be detected in the gases accommodated in the gap between the first polarizer and the second polarizer according to the intensity of the light emitted from the first polarizer or the second polarizer, the method further comprises:
introducing gas into the gap between the first polarizer and the second polarizer.

17. The detecting method according to claim 16, wherein, before the introducing gas into the gap between the first polarizer and the second polarizer, the method further comprises:
discharging gas in the gap between the first polarizer and the second polarizer.

18. The detecting method according to claim 15, wherein, before controlling the light source to emit light and obtaining the concentration of the gas to be detected in the gases accommodated in the gap between the first polarizer and the second polarizer according to the intensity of the light emitted from the first polarizer or the second polarizer, the method further comprises:
detecting the intensity value of the light emitted from the first polarizer or the second polarizer.

19. The detecting method according to claim 15, wherein, before the controlling the light source to emit light and obtaining the concentration of the gas to be detected in the gases accommodated in the gap between the first polarizer and the second polarizer according to the intensity of the light emitted from the first polarizer or the second polarizer, the method further comprises:
providing the photoluminescent layer comprising a phosphor of pyrenes dye, or providing the photoluminescent layer comprising a phosphor of metal porphyrin.

* * * * *